(12) United States Patent
Huang et al.

(10) Patent No.: US 7,696,158 B2
(45) Date of Patent: Apr. 13, 2010

(54) USE OF IL-22 FOR THE TREATMENT OF CONDITIONS OF METABOLIC DISORDERS

(75) Inventors: Yu Liang Huang, Carlsbad, CA (US); Xu Wen Chen, Shanghai (CN)

(73) Assignee: DHY & Co., Ltd., Road Town, Tortola (VG)

( * ) Notice: Subject to any disclaimer, the term of this patent is extended or adjusted under 35 U.S.C. 154(b) by 0 days.

(21) Appl. No.: 11/941,093

(22) Filed: Nov. 16, 2007

(65) Prior Publication Data

US 2008/0069799 A1   Mar. 20, 2008

Related U.S. Application Data

(63) Continuation of application No. 11/813,286, filed as application No. PCT/US2005/028186 on Aug. 8, 2005.

(30) Foreign Application Priority Data

Jan. 4, 2005   (CN)   ................ 2005 1 0023103

(51) Int. Cl.
  *A61K 38/20*   (2006.01)
  *C07K 14/54*   (2006.01)
(52) U.S. Cl. ......................... 514/2; 530/351
(58) Field of Classification Search ............... None
  See application file for complete search history.

(56) References Cited

U.S. PATENT DOCUMENTS

| | | | |
|---|---|---|---|
| 4,849,227 A | 7/1989 | Cho | |
| 5,116,964 A | 5/1992 | Capon | |
| 5,541,087 A | 7/1996 | Lo | |
| 6,274,710 B1 | 8/2001 | Dumoutier et al. | |
| 6,331,613 B1 | 12/2001 | Dumoutier et al. | |
| 6,359,117 B1 | 3/2002 | Dumoutier et al. | |
| 6,551,799 B2 | 4/2003 | Gurney et al. | |
| 7,081,528 B2 | 7/2006 | Dumoutier et al. | |
| 2001/0023070 A1* | 9/2001 | Ebner et al. | 435/69.5 |
| 2003/0012788 A1 | 1/2003 | Renauld et al. | |
| 2003/0023033 A1 | 1/2003 | Dumoutier et al. | |
| 2003/0235561 A1 | 12/2003 | Vandenburgh | |
| 2004/0110189 A1 | 6/2004 | Dumoutier et al. | |
| 2004/0209330 A1* | 10/2004 | Xu et al. | 435/70.21 |
| 2004/0236075 A1 | 11/2004 | Dumoutier et al. | |
| 2005/0271619 A1 | 12/2005 | Dumoutier et al. | |
| 2006/0257408 A1 | 11/2006 | Renauld et al. | |
| 2008/0213881 A1 | 9/2008 | Dumoutier et al. | |

OTHER PUBLICATIONS

Wells, J.A. Additivity of mutational effects in proteins. Biochemistry 29:8509-8517; (1990).*

Ngo et al. Computional complexity protein structure prediction and the levinthal paradox. The Protein Folding Problem and Tertiary Structure, pp. 433-440 and 492-495 (1994).*

Dumoutier et al, Human Interleukin-10-Related T Cell-Derived Inducible Factor: Molecular Cloning and Functional Characterization as an Hepatocyte-Stimulating Factor, PNAS, 2000, 97(18):10144-10149.

* cited by examiner

*Primary Examiner*—Marianne P Allen
*Assistant Examiner*—Regina M DeBerry
(74) *Attorney, Agent, or Firm*—Eagle IP Limited; Jacqueline C. Lui

(57) ABSTRACT

The use of IL-22 for the treatment of metabolic disorders including hyperlipidemia, obesity, hyperinsulinemia and diabetes. IL-22 may also be used in combination with insulin for diabetes.

6 Claims, 7 Drawing Sheets

CTRL                    Treatment

SEQUENCE LISTING

```
<160> NUMBER OF SEQ ID NOS: 8

<210> SEQ ID NO 1
<211> LENGTH: 179
<212> TYPE: PRT
<213> ORGANISM: Homo sapiens

<400> SEQUENCE: 1

Met Ala Ala Leu Gln Lys Ser Val Ser Ser Phe Leu Met Gly Thr Leu
1               5                   10                  15

Ala Thr Ser Cys Leu Leu Leu Leu Ala Leu Leu Val Gln Gly Gly Ala
                20                  25                  30

Ala Ala Pro Ile Ser Ser His Cys Arg Leu Asp Lys Ser Asn Phe Gln
            35                  40                  45

Gln Pro Tyr Ile Thr Asn Arg Thr Phe Met Leu Ala Lys Glu Ala Ser
        50                  55                  60

Leu Ala Asp Asn Asn Thr Asp Val Arg Leu Ile Gly Glu Lys Leu Phe
65                  70                  75                  80

His Gly Val Ser Met Ser Glu Arg Cys Tyr Leu Met Lys Gln Val Leu
                85                  90                  95

Asn Phe Thr Leu Glu Glu Val Leu Phe Pro Gln Ser Asp Arg Phe Gln
                100                 105                 110

Pro Tyr Met Gln Glu Val Val Pro Phe Leu Ala Arg Leu Ser Asn Arg
            115                 120                 125

Leu Ser Thr Cys His Ile Glu Gly Asp Asp Leu His Ile Gln Arg Asn
        130                 135                 140

Val Gln Lys Leu Lys Asp Thr Val Lys Lys Leu Gly Glu Ser Gly Glu
145                 150                 155                 160

Ile Lys Ala Ile Gly Glu Leu Asp Leu Leu Phe Met Ser Leu Arg Asn
                165                 170                 175

Ala Cys Ile

<210> SEQ ID NO 2
<211> LENGTH: 1147
<212> TYPE: DNA
<213> ORGANISM: Homo sapiens

<400> SEQUENCE: 2
cgaccaggtt ctccttcccc agtcaccagt tgctcgagtt agaattgtct gcaatggccg      60
ccctgcagaa atctgtgagc tctttcctta tggggaccct ggccaccagc tgcctccttc     120
tcttggccct cttggtacag ggaggagcag ctgcgcccat cagctcccac tgcaggcttg     180
acaagtccaa cttccagcag ccctatatca ccaaccgcac cttcatgctg gctaaggagg     240
ctagcttggc tgataacaac acagacgttc gtctcattgg ggagaaactg ttccacggag     300
```

```
tcagtatgag tgagcgctgc tatctgatga agcaggtgct gaacttcacc cttgaagaag    360
tgctgttccc tcaatctgat aggttccagc cttatatgca ggaggtggtg cccttcctgg    420
ccaggctcag caacaggcta agcacatgtc atattgaagg tgatgacctg catatccaga    480
ggaatgtgca aaagctgaag gacacagtga aaaagcttgg agagagtgga gagatcaaag    540
caattggaga actggatttg ctgtttatgt ctctgagaaa tgcctgcatt tgaccagagc    600
aaagctgaaa aatgaataac taaccccctt tccctgctag aaataacaat tagatgcccc    660
aaagcgattt tttttaacca aaaggaagat gggaagccaa actccatcat gatgggtgga    720
ttccaaatga acccctgcgt tagttacaaa ggaaaccaat gccacttttg tttataagac    780
cagaaggtag actttctaag catagatatt tattgataac atttcattgt aactggtgtt    840
ctatacacag aaaacaattt atttttttaaa taattgtctt tttccataaa aaagattact    900
ttccattcct ttaggggaaa aaacccctaa atagcttcat gtttccataa tcagtacttt    960
atatttataa atgtatttat tattattata agactgcatt ttatttatat cattttatta   1020
atatggattt atttatagaa acatcattcg atattgctac ttgagtgtaa ggctaatatt   1080
gatatttatg acaataatta tagagctata acatgtttat ttgacctcaa taaacacttg   1140
gatatcc                                                              1147
```

<210> SEQ ID NO 3
<211> LENGTH: 178
<212> TYPE: PRT
<213> ORGANISM: Mus musculus

<400> SEQUENCE: 3

```
Met Ala Val Leu Gln Lys Ser Met Ser Phe Ser Leu Met Gly Thr Leu
1               5                   10                  15

Ala Ala Ser Cys Leu Leu Ile Ala Leu Trp Ala Gln Glu Ala Asn
            20                  25                  30

Ala Leu Pro Val Asn Thr Arg Cys Lys Leu Glu Val Ser Asn Phe Gln
        35                  40                  45

Gln Pro Tyr Ile Val Asn Arg Thr Phe Met Leu Ala Lys Glu Ala Ser
    50                  55                  60

Leu Ala Asp Asn Asn Thr Asp Val Arg Leu Ile Gly Glu Lys Leu Phe
65                  70                  75                  80

Arg Gly Val Ser Ala Lys Asp Gln Cys Tyr Leu Met Lys Gln Val Leu
                85                  90                  95

Asn Phe Thr Leu Glu Asp Val Leu Leu Pro Gln Ser Asp Arg Phe Gln
            100                 105                 110

Pro Tyr Met Gln Glu Val Val Pro Phe Leu Thr Lys Leu Ser Asn Gln
        115                 120                 125

Leu Ser Ser Cys His Ile Ser Gly Asp Asp Gln Asn Ile Gln Lys Asn
    130                 135                 140

Val Arg Arg Leu Lys Glu Thr Val Lys Lys Leu Gly Glu Ser Gly Glu
145                 150                 155                 160

Lys Ala Ile Gly Glu Leu Asp Leu Leu Phe Met Ser Leu Arg Asn Ala
                165                 170                 175

Cys Val
```

<210> SEQ ID NO 4
<211> LENGTH: 1121
<212> TYPE: DNA
<213> ORGANISM: Mus musculus -continued

```
<400> SEQUENCE: 4
cctaaacagg ctctcctctc acttatcaac tgttgacact tgtgcgatct ctgatggctg    60
tcctgcagaa atctatgagt ttttcccttta tggggacttt ggccgccagc tgcctgcttc   120
tcattgccct gtgggcccag gaggcaaatg cgctgcccgt caacaccccgg tgcaagcttg   180 aggtgtccaa cttccagcag ccgtacatcg tcaaccgcac ctttatgctg gccaaggagg   240
ccagccttgc agataacaac acagacgtcc ggctcatcgg ggagaaactg ttccgaggag   300
tcagtgctaa agatcagtgc tacctgatga agcaggtgct caacttcacc ctggaagacg   360
ttctgctccc ccagtcagac aggttccagc cctacatgca ggaggtggta cctttcctga   420
ccaaactcag caatcagctc agctcctgtc acatcagcgg tgacgaccag aacatccaga   480
agaatgtcag aaggctgaag gagacagtga aaaagcttgg agagagtgga gagatcaagg   540
cgattgggga actggacctg ctgtttatgt ctctgagaaa tgcttgcgtc tgagcgagaa   600
gaagctagaa aacgaagaac tgctccttcc tgccttctaa aaagaacaat aagatccctg   660
aatggacttt tttactaaag gaaagtgaga agctaacgtc catcatcatt agaagatttc   720
acatgaaacc tggctcagtt gaaaaagaaa atagtgtcaa gttgtccatg agaccagagg   780
tagacttgat aaccacaaag attcattgac aatatttat tgtcactgat gatacaacag   840
aaaaataatg tactttaaaa aattgtttga aaggaggtta cctctcattc ctttagaaaa   900
aaagcttatg taacttcatt tccatatcca atattttata tatgtaagtt tatttattat   960
aagtatacat tttatttatg tcagtttatt aaatatggatt tatttataga aacattatct  1020
gctattgata tttagtataa ggcaaataat atttatgaca ataactatgg aaacaagata  1080
tcttaggctt taataaacac atggatatca taaaaaaaaa a                      1121

<210> SEQ ID NO 5
<211> LENGTH: 22
<212> TYPE: DNA
<213> ORGANISM: Artificial
<220> FEATURE:
<223> OTHER INFORMATION: Primer

<400> SEQUENCE: 5
gcagaatctt cagaacaggt tc                                              22

<210> SEQ ID NO 6
<211> LENGTH: 22
<212> TYPE: DNA
<213> ORGANISM: Artificial
<220> FEATURE:
<223> OTHER INFORMATION: Primer

<400> SEQUENCE: 6
ggcatctaat tgttatttct ag                                              22

<210> SEQ ID NO 7
<211> LENGTH: 22
<212> TYPE: DNA
<213> ORGANISM: Artificial
<220> FEATURE:
<223> OTHER INFORMATION: Primer

<400> SEQUENCE: 7
ctctcactta tcaactgttg ac                                              22

<210> SEQ ID NO 8
<211> LENGTH: 23
```

```
-continued

<212> TYPE: DNA
<213> ORGANISM: Artificial
<220> FEATURE:
<223> OTHER INFORMATION: Primer

<400> SEQUENCE: 8
gatgatggac gttagcttct cac                                           23
```

USE OF IL-22 FOR THE TREATMENT OF CONDITIONS OF METABOLIC DISORDERS

RELATED APPLICATIONS

This application is a continuation of U.S. application Ser. No. 11/813,286, filed Jul. 3, 2007, which is the National Stage of International application Ser. No. PCT/US2005/028186, filed on 8 Aug. 2005, which claims the benefit of Chinese Patent Application Serial No. 200510023103.0, filed on 4 Jan. 2005, the disclosures of which are all incorporated herein by reference in their entireties.

BACKGROUND OF THE INVENTION

Metabolic disorders including obesity, diabetes, hyperlipidemia hyperglycemia and hyperinsulinemia are complicated syndromes affecting a large population world wide. It is believed that genetic and environmental factors and living habits contributed to the metabolic disorders. These metabolic disorders contribute significantly to the development of coronary heart disease. These is no effective treatment for metabolic disorders such as for obesity and diabetes. Recombinant insulin is widely used to effectively control type I diabetes. But for type II diabetes, treatment with recombinant insulin was not effective since patients developed insulin resistance. Insulin sensitizers are developed for effective for type II diabetes. For hyperlipidemia, current treatments are mainly focused on reducing cholesterol levels in patients by inhibiting cholesterol synthesis or on inhibiting lipid absorption.

FIELD OF THE INVENTION

The invention is related generally to therapeutics and methods of treatment. In particular, the present invention relates to therapeutics and methods of treatment of metabolic disorders, such as obesity, diabetes, hyperlipidemia and hyperinsulinemia.

SUMMARY OF THE INVENTION

It is therefore an object of the present invention to provide an alternative therapeutic and method of treatment for medical conditions associated with nutritional disorders such as obesity, diabetes and related conditions.

The present invention is based on the discovery by the present inventors that interleukin-22 (IL-22) modulates a number of conditions often related to overweight mammals. Accordingly, in one aspect, the invention provides a method for the treatment of hyperlipidemia, including administering to patients with hyperlipidemia a pharmaceutically effective amounts of IL-22 or a functional derivative thereof. In another aspect, the present invention relates to the use of IL-22 or its functional derivative for preparing a medicament for treating hyperlipidemia.

The invention also provides a method for the reduction of serum glucose levels in mammals, including giving mammals with hyperglycemia a pharmaceutically effective amount of IL-22 or a functional derivative thereof. In another aspect, the present invention related to the use of IL-22 or its functional derivative for preparing a medicament for treating hyperglycemia.

The invention also provides the usage of IL-22 in reducing mammalian serum triglyceride levels and the usage of IL-22 in preparing drugs for reducing mammalian serum triglyceride levels. In another aspect, the present invention relates to the use of IL-22 or its functional derivative for preparing a medicament for modulating serum triglyceride levels.

In another aspect, the invention provides a method for the treatment of obesity, including giving obese patients a pharmaceutically effective amount of IL-22. In another aspect, the present invention relates to the use of IL-22 or its functional derivative for preparing a medicament for treating obesity.

The invention also provides a method for losing weight in mammals, including giving mammals of higher than normal weight a pharmaceutically effective amount of IL-22. The invention also provides the usage of IL-22 in losing weight in mammals and the usage of IL-22 in preparing drugs for losing weight in mammals. In another aspect, the present invention relates to the use of IL-22 for preparing a medicament for reducing body weight.

Also in another aspect, the invention provides a method for the treatment of diabetes, including giving patients with diabetes effective amount of IL-22. The invention also provides a method for improving glucose tolerance in mammals, including giving mammals an effective amount of IL-22. The invention also provides the usage of IL-22 in improving mammalian glucose tolerance and the usage of IL-22 in preparing drugs for improving mammalian glucose utilization. In another aspect, the present invention relates to the use of IL-22 or its functional derivative for preparing a medicament for modulating blood glucose levels.

In a further aspect, the present invention relates to the use of a combination of IL-22 and insulin or their respective derivatives for the treatment of the above conditions.

The IL-22 in this invention includes but is not limited to human IL-22, recombinant human IL-22, murine IL-22 and/or recombinant murine IL-22.

As used herein, the terminology "consisting essentially of" refers to a polypeptide which includes the amino acid sequence of IL-22 along with additional amino acids at the carboxyl and/or amino terminal ends while maintaining one or more of the biological activities described herein.

Those skilled in the art can readily determine whether a polypeptide consists essentially of IL-22 under the foregoing definitions by measuring the activity of the peptide or polypeptide using the assays as described below.

In the preferred embodiment, the terminology "consisting essentially of" refers to polypeptides which have 8 or less amino acids in addition to the IL-22 sequence. In the more preferred embodiment, the term means 6 or less amino acids in addition to IL-22. In an even more preferred embodiment, the same terminology refers 4 or less amino acids in addition to IL-22. In another preferred embodiment, the same terminology refers to 2 or 1 amino acid in addition to IL-22.

DETAILED DESCRIPTION OF THE PREFERRED EMBODIMENT

Figure 1:
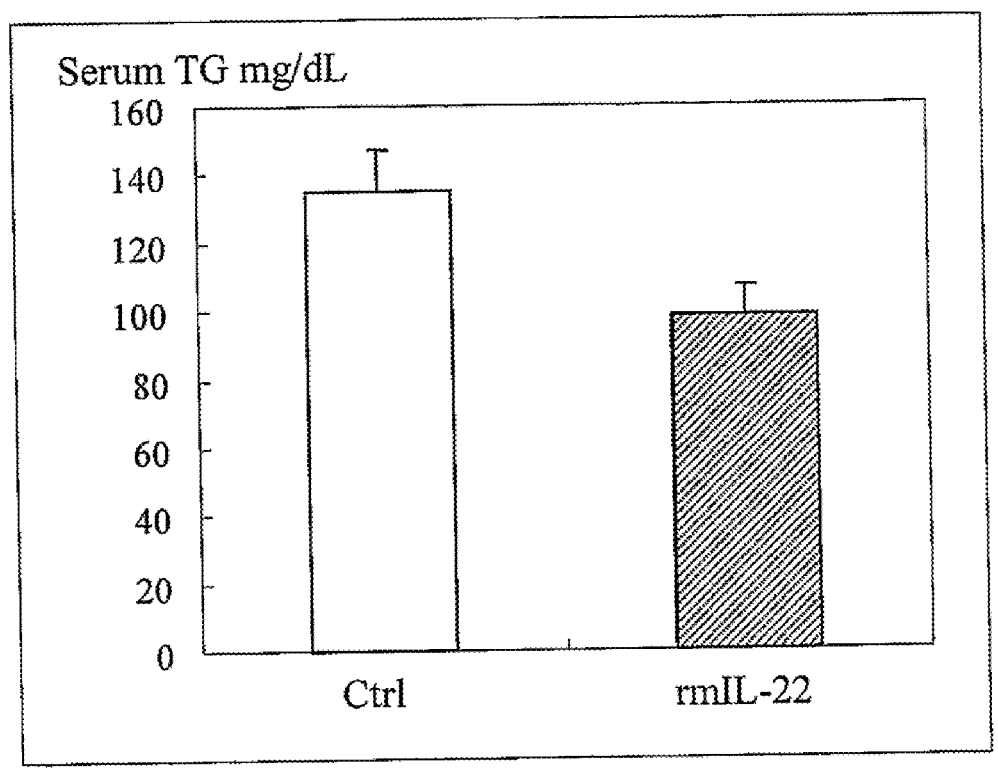
FIG. 1 shows the effect of IL-22 (recombinant mouse IL-22) on total serum triglyceride levels in normal mice.

The following are examples illustrating various aspects of the present invention. All references cited herein are incorporated into the specification in their entirety.

As used herein, the term "metabolic disorders" is used in a broad sense including but not limited to internal imbalances of a human body that may be caused by or aggravated by dietary intake of any sort and multiple environmental and genetic factors. These include medical conditions such as obesity, diabetes, hyperlipidemia, hyperglycemia and hyperinsulinemia.

EXAMPLE 1

Human and Murine IL-22 Gene Cloning

The human IL-22 gene cloning used a similar protocol as described in the original cloning paper by Dumoutier et al., PNAS 2000, 97:10144, and incorporated in its entirety herein. Briefly, human peripheral blood mononuclear cells were cultured for 24 h either with or without anti-human CD3 mAb (Pharmingen Inc., San Diego). Total RNA was extracted by ultracentrifugation, and cDNA was synthesized with dT being the primer according to methods described in Molecular Cloning, 2nd edition, (Sambrook et al, Cold Spring Harbor Laboratory Press, 1989). Human IL-22 with sequence as shown in SEQ ID NO. 1 was amplified by PCR with specific primer pair (5'-GCA GAA TCT TCA GAA CAG GTT C-3' (SEQ ID NO. 5) and 5'-GGC ATC TAA TTG TTA TTT CTA G-3' (SEQ ID NO. 6)). The amplified DNA is cloned to pET21(+) vector and expressed in *E. coli* strain BL21.

The Mouse IL-22 gene cloning: C57BL/6, female mice were injected with LPS. The spleen was obtained after 20 hours. Total RNA was extracted and cDNA was synthesized through dT primer by the same method describe in human IL-22 cloning. Mouse IL-22 was amplified by PCR amplification with specific primer pair (5'-CTC TCA CTT ATC AAC TGT TGA C-3' (SEQ ID NO. 7) and 5'-GAT GAT GGA CGT TAG CTT CTC AC-3' (SEQ ID NO. 8)). The amplified cDNA was cloned to pET21(+) vector and expressed in *E. coli* strain of BL21.

Both hIL-22 (human IL-22) and mIL-22 (murine IL-22) are certified correct by DNA sequence. The sequence of murineIL-22 is shown in SEQ ID NO. 2.

EXAMPLE 2

Recombinant Human IL-22 (RHIL-22) and Recombinant Mouse IL-22 (RMIL-22) Protein Expression The expression of the recombinant proteins used a similar methods as described in the original cloning paper by Dumoutier et al. PNAS vol:97:p10144, 2000 and incorporated herein in its entirety. Briefly *E. coli* strain BL21(+) (Stratagene) was used as the expression host. The host cells were cultured in Luria-Bertani medium with ampicillin (100 mg/ml), chloramphenicol (34 mg/ml), and glucose 2%. Expression of the protein was induced with 1 mM isopropyl-b-D-thiogalactoside. The cell pellet was disrupted with a homogenizer, and the IL-22 inclusion bodies were obtained by centrifugation. Inclusion bodies were washed with TriszHCl 50 mM, NaCl 100 mM, EDTA 1 mM, DTT 1 mM, and sodium deoxycholate 0.5% (wt/vol), pH 8.

Inclusion bodies were solubilized overnight at 4° C. in 8M urea, 50 mM, EDTA 10 mM, and DTT 0.1 mM, pH 6.5. The solution was centrifuged for 1 h at 100,000×g and the supernatant stored at −80° C. until used. The purity of the IL-22 was estimated >90% based on SDS-PAGE and Coomassie blue staining analysis. IL-22 protein was refolded by direct dilution of the solubilized inclusion bodies in the following folding mixture:

IL-22 100 mg/ml, Tris-HCl 100 mM, EDTA 2 mM, L-arginine 0.5 M, reduced glutathion 1 mM, and oxidized glutathion 0.1 mM, pH 8. The solution was incubated for 24 hrs at 4° C. The folding mixture was then purified using a Superdex75 (Amersham Pharmacia Biotech) gel filtration column. The protein was eluted with TriszHCl 20 mM and NaCl, 50 mM, pH 7 and stored at −80° C.

EXAMPLE 3

RMIL-22 Reduced the Total Serum Triglyceride Levels in Normal Mice

Normal mice, C57BL6, 8-12 week, female, body weight: 20-25 g (n=10) were used. The controlled group was injected with a carrier solution (0.1% BSA, Bovine Serum Albumin, PBS, Phosphate Buffered Saline, pH7.0). The tested group was injected with rmIL-22. The dosages were 0, 3, 30, 100, 300 ug/kg/d, once daily, subcutaneous injection continuously for 7 days. Blood samples were collected at different times and the serum was analyzed for the determination of total triglyceride levels.

Result: IL-22 can remarkably reduce the total serum triglyceride levels in normal mice. The effects were dose dependent. FIG. 1 shows the effects of IL-22 on serum triglyceride levels in normal mice after 7 day treatment of normal mice with rmIL-22 at 100 ug/kg. The control mice were injected with carrier. The results show that rmIL-22 treated group had significantly reduced serum triglyceride levels.

EXAMPLE 4

RMIL-22 Reduced Total Serum Triglyceride Levels and Retroperitoneal Fat Weight in Acquired Obese Mice (Normal Aged Mice)

Figure 2:
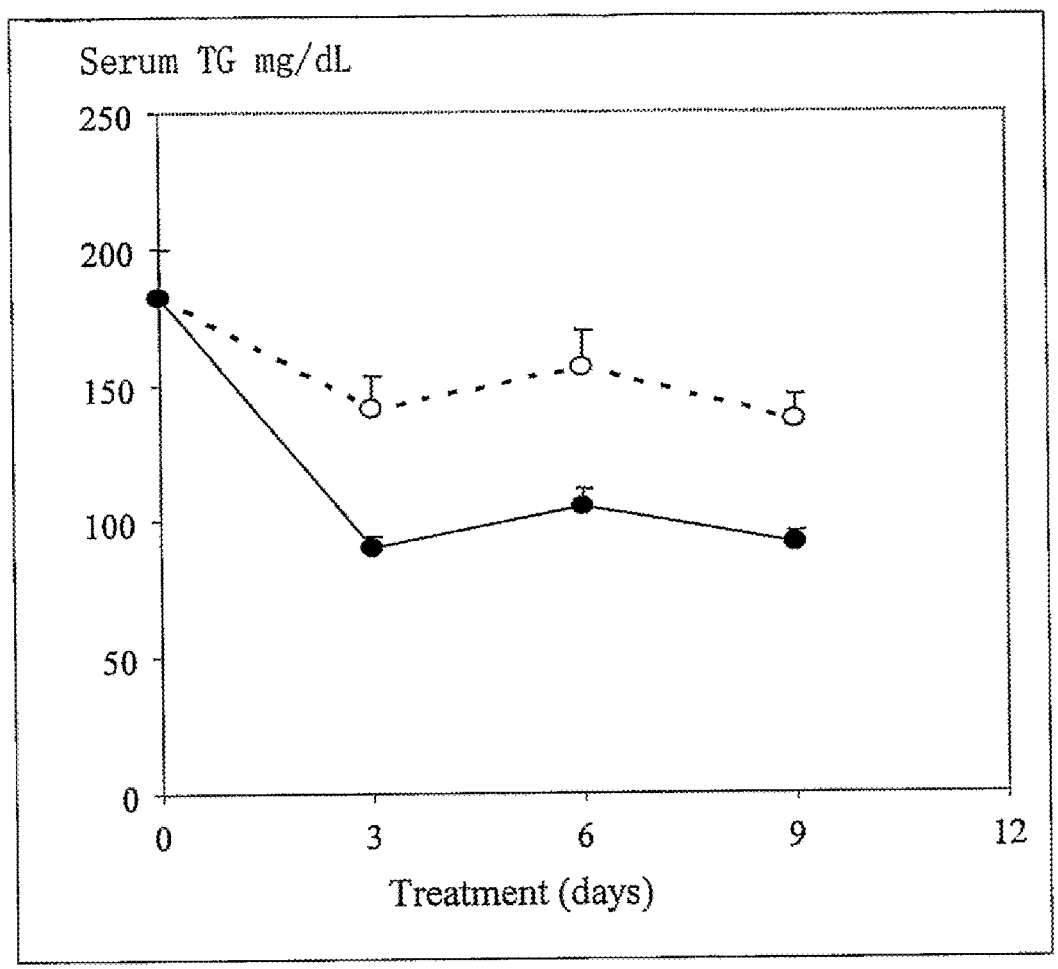
FIG. 2 shows the effect of IL-22 on total serum triglyceride levels in acquired obese mice. Dashed line indicates mice treated with carrier. Solid line indicates nice treated with rmIL-22 (100 ug/kg/day) for 10 days.

18-24 month C57BL6 mice, female (n=10), body weight, 30-40 g were used. The controlled group was injected with carrier (0.1% BSA, Bovine Serum Albumin, PBS, Phosphate Buffered Saline, pH7.0). The tested group was injected with rmIL-22 at 300 ug/kg/d, subcutaneously, once daily, continuously for 9 days. Blood was collected at different time and the serum was analyzed for the determination of total triglyceride levels. For the measurement of retroperitoneal fat weight, mice were treated for 21 days. Animals were sacrificed at the end of treatment. Results show that rmIL-22 can remarkably reduce total serum triglyceride levels in acquired obese mice. FIG. 2 shows the effects of IL-22 on serum triglyceride levels in normal aged mice. Mice were treated with either carrier (dashed line) or rmIL-22 (100 ug/kg/day, solid line) for 10 days. Mice were 16-month old, C57BL6 mice, female (body weight: 38+/−3 gm, n=10). The dotted line indicates controlled group and the solid line indicates tested group. The results are mean+/−sd.

Figure 3A:
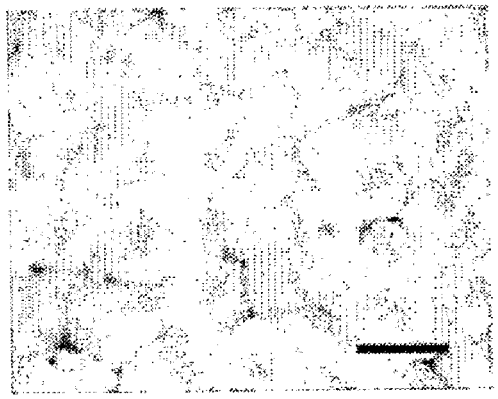
FIGS. 3A and 3B show the effect of IL-22 on the adipocyte of fat tissue in acquired (normal aged) obese mice (FIG. 3B) as compared to the control group (FIG. 3A).
Figure 3B:
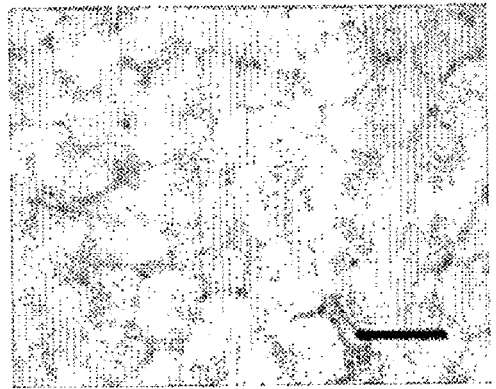

FIG. 3 shows the histological sections of fat tissues of one representative mouse from each treatment groups. Under the same magnification, the size of adipocyte in rmIL-22 treated group (FIG. 3B) was significantly smaller than the control treatment group (FIG. 3A). In addition, the average weight of fat tissues of tested group (110+/−10 mg) is remarkably lower than that of controlled group (175+/−15 mg) (p<0.01).

EXAMPLE 5

IL-22 Reducing Serum Glucose, Triglyceride, Insulin Levels and Body Weight in Hereditary Obese (ob/ob) Mice The ob/ob mice, 8-12 week, female, body weight 35-50 g were used. The controlled group was injected with carrier (0.1% BSA, Bovine Serum Albumin, PBS, Phosphate Buffered Saline, pH7.0). The tested group was injected with rmIL-22 300 ug/kg/d subcutaneously, once daily, continuously for 14 days. Body weight (BW) was recorded. The serum levels for glucose, triglyceride and insulin were determined.

Figure 4:
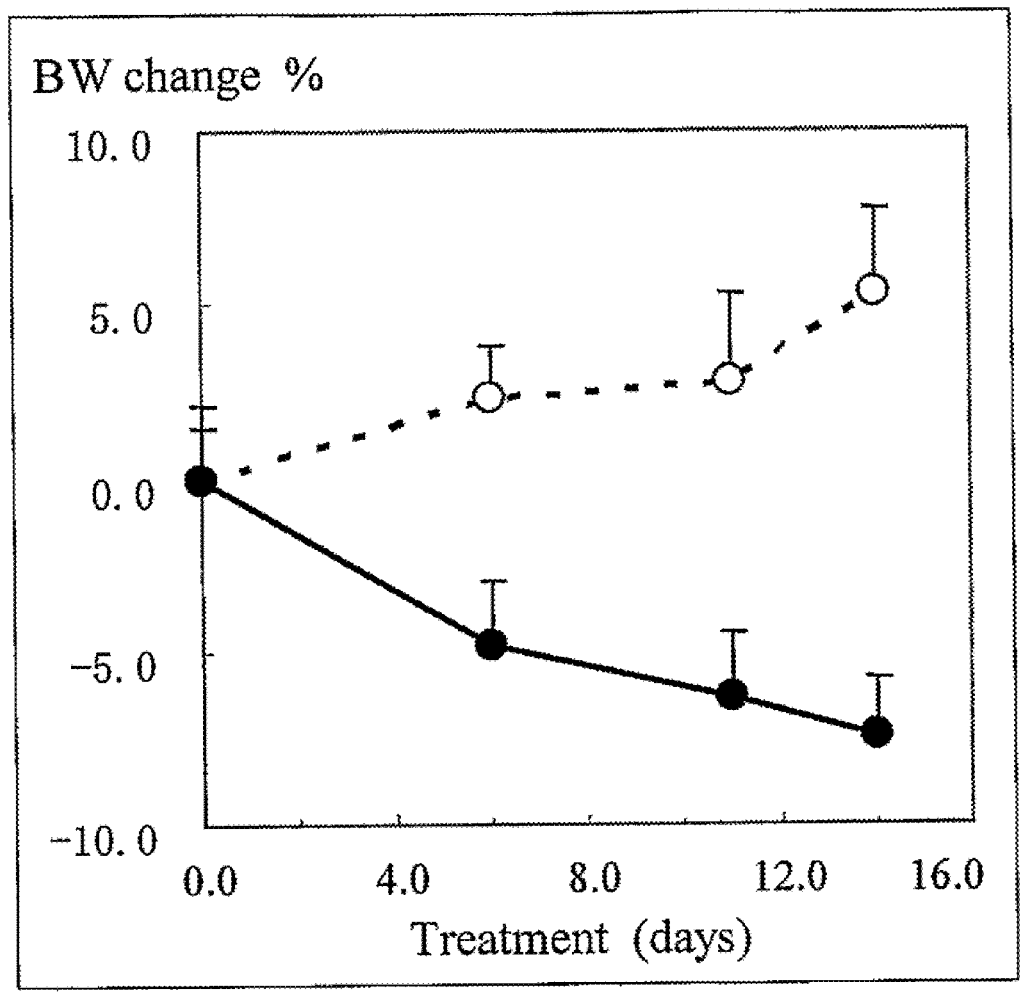
FIG. 4 shows the effect of IL-22 on body weight in hereditary (ob/ob) obese mice. Dashed line indicates controlled group. Solid line indicates test group.
Figure 5:
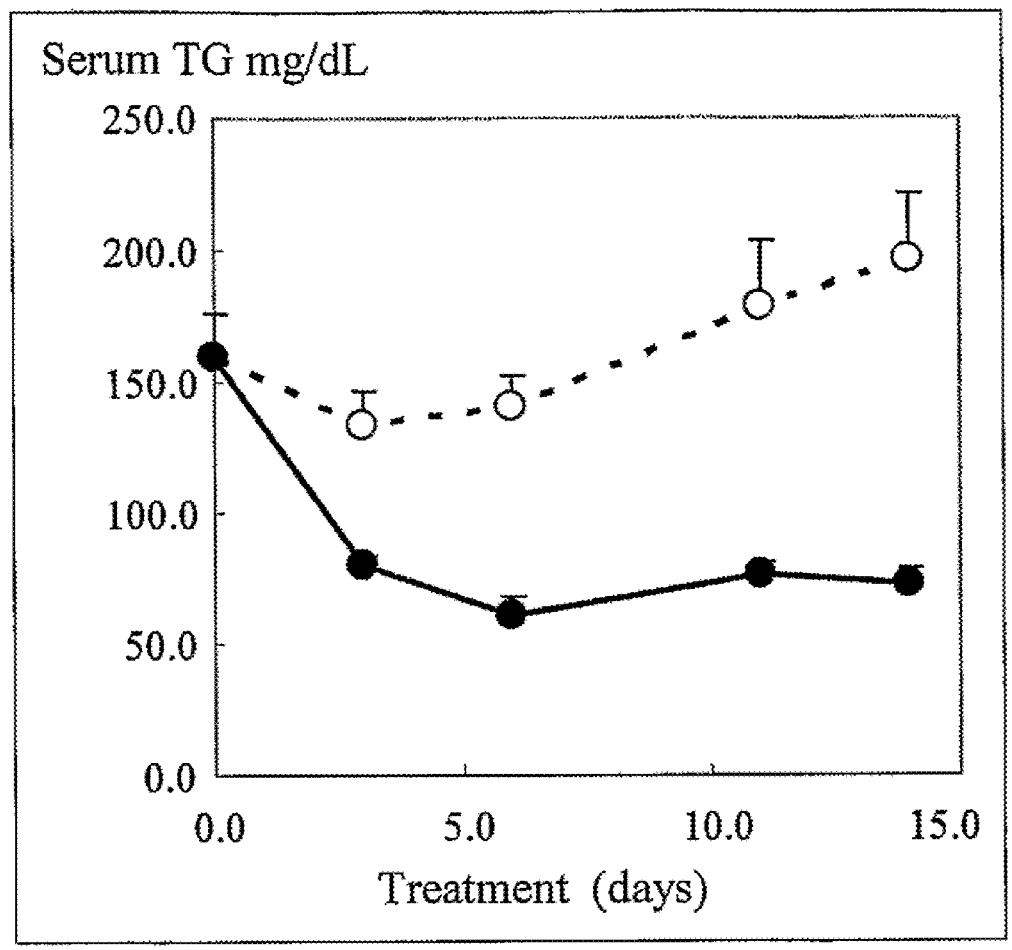
FIG. 5 shows the effect of IL-22 on total serum triglyceride levels in hereditary (ob/ob) obese mice. Dashed line indicates mice treated with carrier. Solid line indicates mice treated with rmIL-22 (300 ug/kg/day) for 2 weeks.

Results showed that rmIL-22 was able to remarkably reduce serum glucose, insulin levels in ob/ob mice. FIG. 4 shows the body weight in ob/ob mice treated with rmIL-22. The dotted line in FIG. 4 indicates controlled group and the solid line indicates tested group. In the carrier treated mice, the body weight increased more than 5% during the 14 day treatment. In rmIL-22 treated mice, the body weight reduced more than 7% during the 14 day treatment. The data show that rmIL-22 can cause reduction of body weight in hereditary obese mice. FIG. 5 shows the effects of IL-22 on serum triglyceride levels in ob/ob mice. Dashed line indicates mice treated with carrier and the solid line indicates mice treated with rmIL-22 (300 ug/kg/day) for 2 weeks (n=10). The data shows that IL-22 can cause reduction of total serum triglyceride levels in hereditary obese mice.

EXAMPLE 6

RMIL-22 Improving Glucose Tolerance and Insulin Sensitivity in Mice

Figure 6:
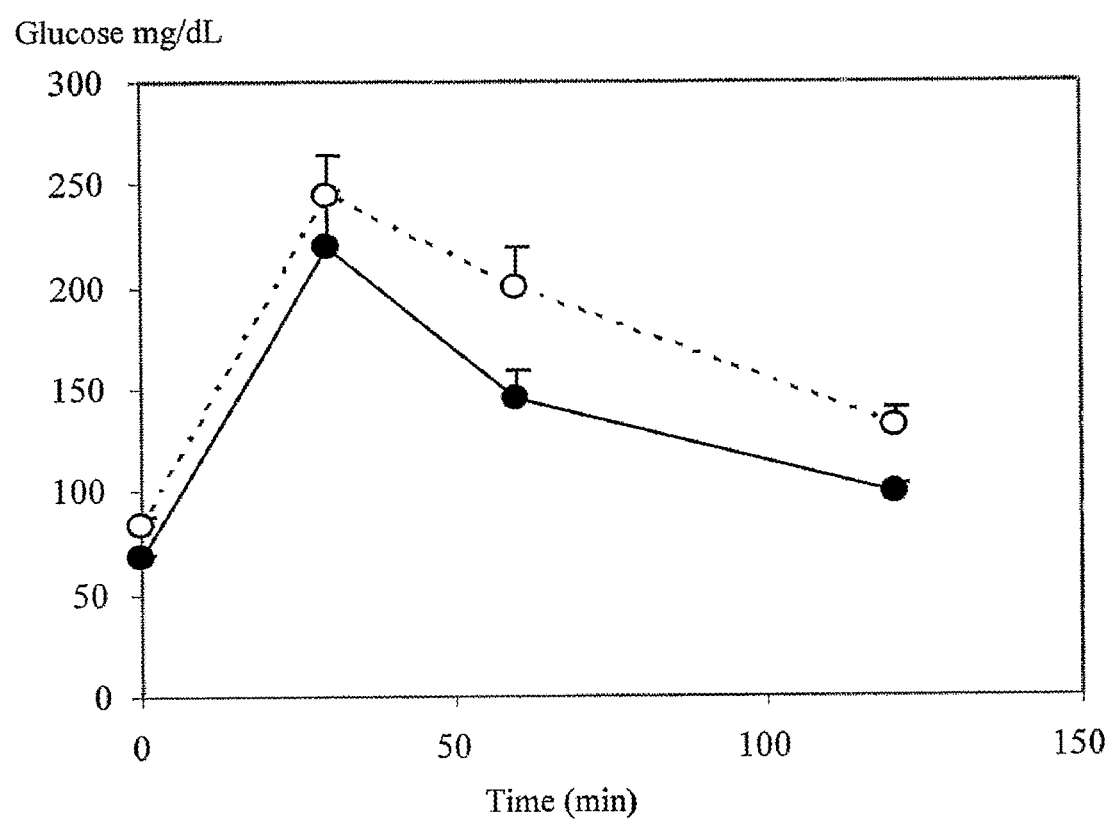
FIG. 6 shows the effect of IL-22 on glucose tolerance in mice. Dashed line Indicates blood glucose levels in mice treated with carrier. Solid line indicates blood glucose levels in mice treated with rmIL-22 (300 ug/kg/day) for 2 weeks.

The glucose endurance and insulin sensitivity tests were performed using 8-12 week C57BL6 mice, female, body weight: 20-25 g with and without rmIL-22 treatment. The controlled group was injected with carrier (0.1% BSA, Bovine Serum Albumin, PBS, Phosphate Buffered Saline, pH7.0). The rmIL-22 treatment group was injected with rmIL-22 300 ug/kg/d, once daily, subcutaneous injection continuously for 14 days. At the end of treatment, mice were fasted over night. Glucose was administered by intraperitoneal injection to each animal at 2 mg/g (body weight). Blood glucose concentration was determined at 30, 60 and 120 mins post Glucose injection. FIG. 6 shows that IL-22 enhanced the glucose utilization in mice in a glucose tolerance test. Dashed line indicates blood glucose levels in mice treated with carrier. Solid line indicates glucose levels in mice treated with rmIL-22 (300 ug/kg/day) for 2 weeks (n=10). Glucose levels are significantly different between the two groups at 60 minutes and 120 minutes (p<0.01).

Figure 7:
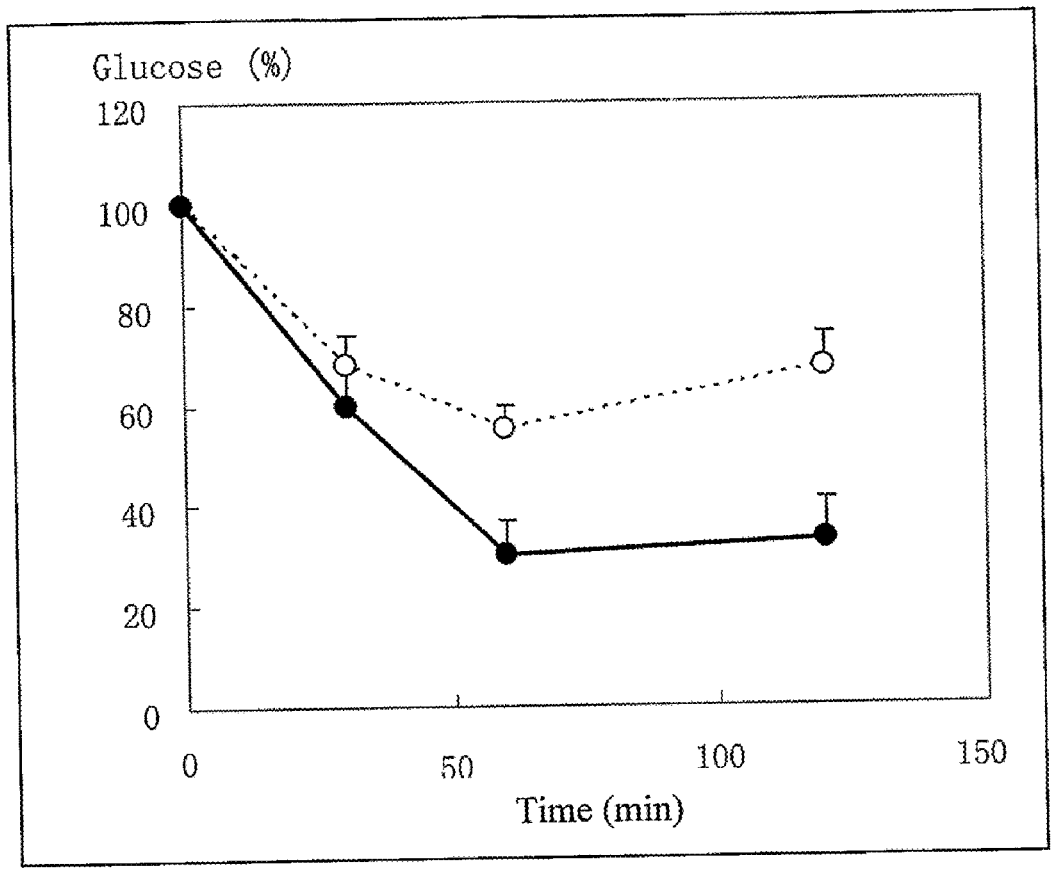
FIG. 7 shows the effect of IL-22 on insulin sensitivity in mice. Dashed line indicates controlled group. Solid line indicates mice treated with rmIL:22 (100 ug/kg/day) for 2 weeks.

FIG. 7 shows that rmIL-22 can increase the insulin sensitivity in mice. The dotted line indicates controlled group and the solid line indicates rmIL-22 (300 ug/kg/day) treated group for 2 weeks. Both groups of animals were injected with the same dosage of insulin, and the blood glucose levels were measured after insulin treatment. Glucose levels, shown as percentage change in rmIL-22 treated group are significantly lower than the control treatment group at 60 minutes and 120 minutes (p<0.01).

While the various aspects of the present invention have been illustrated using the examples described above, it is clear that there are many other ways that the present invention may be practiced given the guidance provided herein. For example, the hosts that can be used to express or clone IL-22 in this invention include prokaryotic cells, yeast cells or eukaryotic cells. The proper prokaryotic cells include but are not limited to G+/G− bacteria, such as *E. coli*. These are available *E. coli* strains: K12 MM294 (ATCC 31,446), X1776 (ATCC 31,537), W3110 (ATCC 27,325) and K5 772 (ATCC 53,635), JM109, DH5, B stains, B834, BL21, BLR et al. Other proper prokaryotic cells include: *Erwinia, Klebsiella, Proteus, Salmonella*, such as *Salmonella typhimurium, Serratia, Shigella, B. subilis, B. licheniformis, Pseudomonas, Streptomyces*. Among numbers of available *E. coli* strains, *E. coli*. W3110 is the first to be chosen for recombinant DNA products.

Besides prokaryotic cells, eukaryotic cells as filamentous fungi or yeast cells are also proper for the expression or clone of IL-22 in this invention. These are proper strains: *Saccharomyces, Schizosaccharomyces pombe* (Beach and Nurse, Nature, 290:140-142 (1981); EP 139,383), *Kluyveromyces* hosts (U.S. Pat. No. 4,943,529; Flee et al., Bio/Technology, 9:968-975 (1991), such as *K. lactis* (MW 98-8C, CBS683, CBS4574; Louvencourt et al., J. Bacteriol., 154(2):737-742 (1983)), *K. fragilis* (ATCC 12,424), *K. waltii* (ATCC 56,500), *K. drosophilarum* (ATCC 36,906; Van den Berg et al., Bio-Technology, 8:135-139 (1990)), *K. thermotolerans, K. marxianus; yarrowia* (EP 244,234), *Neurospora crassa* (Case et al., Proc. Natl. Acad. Sci. USA, 76:5259-5263 (1979)), *schwanniomyces* as *Schwanniomyces occidentalis* (EP 394, 538), filamentous fungi as *Neurospora, penicillium, Tolypocladium* (WO 91/00357), *Aspergillus* as *A. nidulans* (Balance et al., Biochem. Biophys. Res. Commum., 112:284-289 (1983); Tilburn et al., Gene, 26:205-221 (1983); Yelton et al., Proc. Natl. Acad. Sci. USA, 81:1470-1474 (1984)), *A. niger* (Kelly and Hynes, EMBO J., 4:475-479 (1985)). Methylotropic yeasts are also proper, including those ones that can grow on methanol, such as *Hansenula, Candida, kloeckera, Pichia, Saccharomyces, Torulopsis, Rhodotorula*. (C. Anthony, The Biochemistry of Methylotrophs, 269 (1982)).

The host used to express glycosylated IL-22 in this invention are preferably from multicell organisms. The Invertebrate cells include insect cells as *Drosophila* S2 and *Spodoptera* Sf9 and plant cells. The proper mammalian cells include CHO, COS cells, especially CV1 strain transformed by SV40 (COS-7, ATCC CRL 1651), human embryo renal cells 293 (Graham et al., J. Gen. Virol., 36:59-74 (1977)), CHO/-DHFR (Urlaub and Chasin, Proc. Natl. Acad. Sci. USA, 77:4216-4220 (1980)), murine testes trophoblast cells (TM4, Mather, Biol. Reprod., 23:243-251 (1980)), human pulmonary cells (WI38, ATCC CCL 75), human liver cells (hep G2, HB 8065), murine mastocarcinoma cells (MMT 060562, ATCC CCL 51). Technicians in this field should know how to select proper host cells.

After transfection or conversion by the vector, the above host cells can be cultured in common nutrient media. The modified media are fit for inducing the promoter, selecting transformant or amplifying IL-22 encoded gene sequence. Technicians in this field should know the culture conditions, such as media, temperature, pH, et al. Detailed techniques can be seen in Mammalian Cell Biotechnology: A Practical Approach, M. Butler, ed. (IRL Press, 1991) and Sambrook et al., supra.

The method of eukaryotic transfection and prokaryotic conversion, such as CaCl2 method, calcium phosphate precipitation, liposome intermediary or electroporation are known to those skilled in the art. For example, CaCl2 method (Sambrook et al., supra.) or electroporation are fit for prokaryotic cells. The infection of *Agrobacterium tumefaciens* is fit for some plant cells (Shaw et al., Gene, 23:315-330 (1983) and WO 89/05859). Calcium phosphate precipitation is fit for mammalian cells (Graham and van der Eb, Virology, 52; 456-457 (1978)). Detailed techniques on yeast cell conversion can be seen in Van Solingen et al., J. Bact., 130:946-947 (1977); and Hsiao et al., Proc. Natl. Acad. Sci. (USA), 76:3829-3833 (1979). Other method such as microinjection of nucleic acid, electroporation, bacterial protoplast fusion with intact cells et al are also fitful. Techniques concerned with conversion of mammalian cells can be seen in Keown et al., Methods in Enzymology, 185:527-537 (1990); and Mansour et al., Nature, 336:348-352 (1988).

The DNA sequence encoding IL-22 in this invention can be inserted into a replicable vector to clone the gene or express the protein. All the vectors, such as plasmid, cosmid, virion or bacteriophage are publicly available. Applying common techniques in this field, technicians can insert the DNA sequence encoding IL-22 into appropriate restriction endonuclease sites. A replicable vector usually contains but is not limited to following parts: one or more signal sequence, one origin of replication, one or more marker gene, one enhancer element, one promoter, and one transcription termination sequence. Applying standard ligation techniques in this field, technicians can construct an appropriate replicable vector containing one or more above parts.

The IL-22 in this invention can be directly expressed through recombinant DNA, and it can also be produced through fusion of polypeptides. The later can be a signal sequence localized in the mature protein or N-terminal of the polypeptide. It can also be other fragments with special cutting sites localized in the mature protein or N-terminal of the polypeptide. Usually, the signal sequence is one part of the above replicable vector, or one part of DNA sequence encoding IL-22 in this invention. The signal sequence can be prokaryotic one, such as ALP, penicillinase, lpp, etc. In yeast secretion, the signal sequence can be yeast invertase leader, a agent leader sequence or ALP leader sequence, etc. In mammalian expression, the mammalian signal sequence can be directly used to secrete the target protein.

Both the expression vector and the clone vector have a piece of DNA sequence, which can make the vector replicate in one or more hosts. The sequence corresponding with bacteria, yeast and virus hosts are known to technicians in this field (Molecular Cloning, 2nd edition, (Sambrook et al, Cold Spring Harbor Laboratory Press, 1989).

Both the expression vector and the clone vector have a piece of selecting gene, that is "selecting marker". Typical protein expressed by selecting gene has resistance to some antibiotics and toxin, is able to remedy auxotrophic deficiencies and supplement some key nutrient factors that complex media can not provide.

The selecting gene suitable for mammalian host cells may be able to distinguish the host cells containing IL-22 encoding gene, such as DHFR or thymidine kinase. The proper host cell with wide DHFR as selecting gene is CHO strain without DHFR activity. The culture method can be seen in Urlaub et al., Proc. Natl. Acad. Sci. USA, 77:4216-4220 (1980). The selecting gene suitable for yeast cells is trp1 gene expressed in yeast plasmid Yrp7 (Stinchcomb et al., Nature, 282:39-43 (1979); Kingsman et al., Gene, 7:141-152 (1979); Tschumper et al., Gene, 10:157-166 (1980)). Trp1 gene can be used to select yeast mutation strain which can not grow on tryptophan, such as ATCC No. 44047 or PEP4-1 (Jones, Genetics, 85:22-33 (1977)).

Both expression vector and clone vector usually have a promoter that can be ligated to the IL-22 encoding DNA sequence, which can direct mRNA synthesis. Promoters corresponding with all kinds of hosts should be known to technicians in this field. The promoters suitable for prokaryotic hosts include beta-lactamase and lactose promoter system (Chang et al., Nature, 275:615 (1978); Goeddel et al., Nature, 281; 544-548 (1979)), ALP and trp promoter system (Goeddel, Nucleic Acids Res., 8:4057-4074 (1980); EP 36,776), hetero-promoter as tac promoter (deBoer et al., Proc. Natl. Acad. Sci. USA, 80:21-25 (1983)). Bacterial promoter also has a piece of Shine-Dalgarno sequence that can be ligated to the IL-22 encoding sequence.

Promoters suitable for yeast host include 3-phosphoglyceric phosphokinase promoter (Hitzeman et al., J. Biol. Chem., 255:12073-12080 (1980)) or other glycolysis enzyme promoters (Hess et al., J. Adv. Enzyme Reg., 7:149-167 (1968); Holland, Biochemistry, 17:4900-4907 (1978)), such as enolase, glyceraldehydes-3-phosphatedehydrogenase, hexokinase, pyruvate decarboxylase, fructose diphosphatase, et al.

Some other inducible yeast promoter can regulate transcription according to different growing conditions. Detailed description can be seen in U.S. Pat. Nos. 5,063,154 and 6,221,630.

Promoters can control the transcription of IL-22 encoding gene on the replicable vector in mammalian host cells. The promoters include ones from certain viral genome, foreign mammalian promoters and heat shock protein promoter, et al. However, those promoters should be compatible with the expression system of the host.

The transcription of the IL-22 encoding sequence in eukaryotic expression system can be enhanced through the insertion of enhancer into the replicable vectors. Enhancer is a kind of cis-acting element of DNA molecules, usually 10-300 bp, which can enhance the transcription of DNA molecules by acting on the promoters. Numbers of enhancers have been known from mammalian gene, and most widely used enhancers are from eukaryotic viral cells. The enhancers can be inserted into 5' or 3' terminal of the IL-22 encoding sequence on the replicable vectors but 5' terminal is first chosen.

The expression vectors in eukaryotic host cells (yeasts, fungi, insects, plants, animals, human, or other multicell organisms) also contain the DNA sequence for terminating transcription and stabilizing mRNA. This kind of sequence is usually from the 5' or 3' terminal of non-translated region in eukaryotic cells or viral DNA or cDNA. Other methods, vectors and hosts can be seen in Gething et al., Nature, 293: 620-625 (1981); Mantei et al., Nature, 281:40-46 (1979); EP 117,060; EP 117,058.

Gene marking and gene therapy may be performed using the protocols taught by Anderson et al., Science 256, 808-813 (1992). The gene delivery system may include various viral-based vectors including retroviral vectors, adenoviral vectors or AAV, director plasmid delivery, of liposome-mediated or receptor-mediated gene delivery (Dzau et al., Trends in Biotechnology 11, 205-210, 1993).

The IL-22 encoding DNA sequence in this invention can be used on gene therapy, in the course of which the IL-22 gene is transduced into cells in order to express the product having therapeutic effects, such as replacing the former defective gene. Gene therapy includes traditional therapy, that is long term effects through one time therapy and giving gene therapy drugs. The later includes giving effective DNA or mRNA one time or several times.

The IL-22 in this invention can be used as drugs. Technicians in this field can prepare several kinds of effective formulation according to usual method, which contains effective amount of IL-22 and medicinal carriers.

When prepared as lyophilization or liquid, the medicinal composition in this invention should be added some other carrier, excipient, stabilizer, et al that are acceptable physiologically for the convenience of preservation such as described in Remington's Pharmaceutical Sciences 16th edition, Osol, A., Ed. (1980)), the disclosure of which is incorporated by reference herein in its entirety. The dosage and concentration of the carrier, excipient and stabilizer should be safe for human, mice and other mammals.

In one aspect, the formulation comprises an effective amount of IL-22 and a physiologically acceptable carrier, diluent, or excipient, or a combination thereof.

The term "pharmaceutical composition" or "pharmaceutical formulation" refers to a mixture of IL-22 with other chemical components, such as diluents or carriers. The pharmaceutical composition facilitates administration of the I:-22 to an organism. Multiple techniques of administering the formulation may be used including, but not limited to, oral, injection, aerosol, parenteral, and topical administration.

The term "carrier" defines a chemical compound that facilitates the incorporation of the IL-22 into cells or tissues. For example dimethyl sulfoxide (DMSO) is a commonly utilized carrier.

The term "diluent" defines chemical compounds diluted in water that will dissolve the IL-22 as well as stabilize the biologically active form of the IL-22. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a pharmaceutically active substance.

The term "physiologically acceptable" defines a carrier or diluent that does not abrogate the biological activity and properties of the IL-22.

The pharmaceutical compositions described herein can be administered to a human patient per se, or in pharmaceutical compositions where they are mixed with other active ingredients, as in combination therapy, or suitable carriers or excipient(s). Techniques for formulation and administration of the formulations described in the instant application may be found in "Remington's Pharmaceutical Sciences," Mack Publishing Co., Easton, Pa., 18th edition, 1990, the disclosure of which is incorporated herein by reference in its entirety.

Suitable routes of administration may, for example, include oral, rectal, transmucosal, or intestinal administration; parenteral delivery, including intramuscular, subcutaneous, intravenous, intramedullary injections, as well as intrathecal, direct intraventricular, intraperitoneal, intranasal, or intraocular injections.

Alternately, one may administer the IL-22 formulation in a local rather than systemic manner, for example, via injection directly in the renal or cardiac area, often in a depot or sustained release formulation. Furthermore, one may administer the IL-22 in a targeted drug delivery system, for example, in a liposome coated with a tissue-specific antibody. The liposomes will be targeted to and taken up selectively by the organ.

The pharmaceutical compositions of the present invention may be manufactured in a manner that is itself known, e.g., by means of conventional mixing, dissolving, granulating, dragee-making, levigating, emulsifying, encapsulating, entrapping or tabletting processes.

Pharmaceutical compositions for use in accordance with the present invention thus may be formulated in conventional manner using one or more physiologically acceptable carriers comprising excipients and auxiliaries which facilitate processing of IL-22 into preparations which can be used pharmaceutically. Proper formulation is dependent upon the route of administration chosen. Any of the well-known techniques, carriers, and excipients may be used as suitable and as understood in the art; e.g., in Remington's Pharmaceutical Sciences, above.

For injection, the IL-22 of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the IL-22 can be formulated readily by combining it with pharmaceutically acceptable carriers well known in the art. Such carriers enable the IL-22 to be formulated as tablets, pills, dragees, capsules, liquids, gels, syrups, slurries, suspensions and the like, for oral ingestion by a patient to be treated. Pharmaceutical formulations for oral use can be obtained by mixing one or more solid excipient with IL-22, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of IL-22 doses.

Pharmaceutical preparations which can be used orally include push-fit capsules made of gelatin, as well as soft, sealed capsules made of gelatin and a plasticizer, such as glycerol or sorbitol. The push-fit capsules can contain the IL-22 in admixture with filler such as lactose, binders such as starches, and/or lubricants such as talc or magnesium stearate and, optionally, stabilizers. In soft capsules, the IL-22 may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the IL-22 for use according to the present invention is conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the IL-22 and a suitable powder base such as lactose or starch.

IL-22 may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the IL-22 in water-soluble form. Additionally, in some embodiments, suspensions of the IL-22 may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the IL-22 to allow for the preparation of highly concentrated solutions.

Alternatively, the IL-22 may be in powder form for constitution with a suitable vehicle, e.g., sterile pyrogen-free water, before use.

The IL-22 may also be formulated in rectal compositions such as suppositories or retention enemas, e.g., containing conventional suppository bases such as cocoa butter or other glycerides.

In addition to the formulations described previously, the IL-22 may also be formulated as a depot preparation. Such long acting formulations may be administered by implantation (for example subcutaneously or intramuscularly) or by intramuscular injection. Thus, for example, the IL-22 may be formulated with suitable polymeric or hydrophobic materials (for example as an emulsion in an acceptable oil) or ion exchange resins, or as sparingly soluble derivatives, for example, as a sparingly soluble salt.

If desired, the formulation may comprise a cosolvent system comprising benzyl alcohol, a nonpolar surfactant, a water-miscible organic polymer, and an aqueous phase. A common cosolvent system used is the VPD co-solvent system, which is a solution of 3% w/v benzyl alcohol, 8% w/v of the nonpolar surfactant Polysorbate 80™, and 65% w/v polyethylene glycol 300, made up to volume in absolute ethanol. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of POLYSORBATE 80™; the fraction size of polyethylene glycol may be varied; other biocompatible polymers may replace polyethylene glycol, e.g., polyvinyl pyrrolidone; and other sugars or polysaccharides may substitute for dextrose.

Alternatively, if desired other delivery systems may be used. Liposomes and emulsions are well known examples of delivery vehicles or carriers which may be utilized. Certain organic solvents such as dimethylsulfoxide also may be employed, although usually at the cost of greater toxicity. In some embodiments, the IL-22 may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the IL-22 for a few weeks up to over 100 days. Depending on the chemical nature and the biological stability of the therapeutic reagent, additional strategies for protein stabilization may be employed.

In some embodiments, the IL-22 may be provided as a salt with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free acid or base forms.

Pharmaceutical compositions suitable for use in the present invention include compositions where the IL-22 is contained in an amount effective to achieve its intended purpose. More specifically, a therapeutically effective amount means an amount of IL-22 effective to prevent, alleviate or ameliorate symptoms of disease or prolong the survival of the subject being treated. Determination of a therapeutically effective amount is well within the capability of those skilled in the art.

The exact formulation, route of administration and dosage for the IL-22 compositions of the present invention can be chosen by the individual physician in view of the patient's condition. (See e.g., Fingl et al. 1975, in "The Pharmacological Basis of Therapeutics", Ch. 1 p. 1). The dosage may be a single one or a series of two or more given in the course of one or more days, as is needed by the patient. In some embodiments, a suitable human dosage can be inferred from $ED_{50}$ or $ID_{50}$ values, or other appropriate values derived from in vitro or in vivo studies, as qualified by toxicity studies and efficacy studies in animals.

Dosage amount and interval may be adjusted individually to provide plasma levels of the IL-22 which are sufficient to maintain the modulating effects, or minimal effective concentration (MEC). If desired, the MEC can be estimated from in vitro data. Dosages necessary to achieve the MEC will depend on individual characteristics and route of administration. However, HPLC assays or bioassays can be used to determine plasma concentrations.

Dosage intervals can also be determined using MEC value. In some embodiments, the formulations are administered using a regimen which maintains plasma levels above the MEC for 10-90% of the time, preferably between 30-90% and most preferably between 50-90%.

In cases of local administration or selective uptake, the effective local concentration of the IL-22 may not be related to plasma concentration.

The amount of composition administered will, of course, be dependent on the subject being treated, on the subject's weight, the severity of the affliction, the manner of administration and the judgment of the prescribing physician.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions according to the present invention formulated in a compatible pharmaceutical carrier may also be prepared, placed in an appropriate container, and labeled for treatment of an indicated condition.

In some embodiments, the composition may include buffer, antioxidant, small polypeptide, proteins such as serum albumin, gelatin or immunoglobulin, hydrophilic polymers such as PVP, amino acids, such as aminoacetate glutamate salt, etc., glycose, biose and other carbohydrate as glucose, mannose or dextrin, chelate agent as EDTA, sugar alcohols as mannitol, sorbitol, counterions as Na+, and/or nonionic surfactants such as TWEEN™, PLURONICS™ or PEG, etc.

Preferably, the preparation containing IL-22 in this invention is sterilized before injection. This procedure can be done using sterile filtration membranes before or after lyophilization and reconstitution.

The medicinal composition is usually filled in a container with sterile access port. The medicinal composition in this invention can be injected through normal ways, including but not limited to intravenous, intra-abdominal, intracephalic, intramuscular, intraocular, intra-arterial, locally or through sustained release systems.

The dosage and concentration can be adjusted according to actual situation. Technicians in this field should know how to choose proper dosage and injection ways according to actual situation. The animal tests in this invention have provided believable direction for the effective amount in human body. The adjustment principle of between different species can be seen in Mordenti, J. and Chappell, W. "The use of interspecies scaling in toxicokinetics" In Toxicokinetics and New Drug Development, Yacobi et al.; Pergamon Press, New York 1989, pp. 42-96.

When the IL-22 is injected in mammals, the usual dosage is 1 ng/kg-100 mg/kg body weight daily, optimally 10 ug/kg/d-100 ug/kg/d. The dosage should be adjusted according to different injection way. The direction can be seen in U.S. Pat. Nos. 4,657,760; 5,206,344; or 5,225,212. Predictably, different IL-22 preparations effect on different diseases. When the effecting target (organ or tissue) changes, the injection way should be adjusted accordingly.

The micro-capsule containing IL-22 can be used as sustained release system. Techiques of micro-capsule sustained release system of recombinant protein have been successfully adopted on rhGH, rhIFN, IL-2 and MNrgp120 (Johnson et al., Nat. Med., 2:795-799 (1996); Yasuda, Biomed. Ther 27:1221-1223 (1993); WO 97/03692, WO 96/40072, WO 96/07399; U.S. Pat. No. 5,654,010).

The sustained release system of IL-22 in this invention can be prepared with PLGA which is biologically compatible and easily degraded. Lactate and hydroxyacetate, the degrading products of PLGA, can be cleared quickly in human body. Furthermore, the degrading ability can be different from several months to several years according to its different molecule and composition (Lewis, "Controlled release of bioactive agents form lactide/glycolide polymer," in: M. Chasin and R. Langer (Eds.), Biodegradable Polymers as Drug Delivery Systems (Marcel Dekker: New York, 1990), pp. 1-41)).

The IL-22 in this invention can be modified with activated PEG with, for example, but not limited to, molecular weight being 5,000-100,000 for the purpose of prolonging its half-life time. It can also be prepared as Chimeric Molecule or Fusion Protein, for the purpose of enhancing its biological activity or prolonging its half-life time. Detailed techniques can be seen in Greenwald et al., Bioorg. Med. Chem. Lett. 1994, 4:2465-2470; Caliceti et al., IL Farmaco, 1993, 48:919-932, etc.

IL-22 in this invention can be prepared as a chimeric molecule or fusion protein for the purpose of enhancing its biological activity or prolonging its biological half-life time. Covalently modified IL-22 is also included in this invention. Chemically covalent modification includes modifying N or C terminal or adding a chemical molecule to the other amino acid. It also includes modification of amino acid sequence, modification of the glycosylation of IL-22 itself.

Other preparing techniques as nanotechnology preparation (U.S. 60/544,693), spraying preparation (for example as taught in CN00114318.2, PCT/CN02/00342), inhaling preparation, et al. are also included in this invention. All cited references are hereby incorporated in their entirety.

The polypeptide used for the above experiments contains the sequence as shown in SEQ ID NO. 1 using the nucleic acid sequence as shown in SEQ ID NO. 3. Nevertheless, it is clear that SEQ ID NOs. 1-4 are only some embodiments of the present invention and that the same principle of the present invention can also be applied to other functionally equivalent peptides that have been modified without affecting the biological function of IL-22. For example, those with conservative amino acid substitutions (i.e. amino acids within the same biochemical type such as hydrophobic, hydrophilic, positive or negatively charged groups). Those peptides that have one or more of the above modification and yet retain the activity described in the present invention are referred to as functional variants. Other peptides that have at least 95%, 90%, 85%, 80%, 75%, 70%, 65%, 60%, 55%, 50%, 45%, 40%, 35% or 30% amino acid or nucleotide sequence identity to one of SEQ ID NOs. 1-4 and retain one or more activities of IL-22 or encode a polypeptide which retains one or more activities of IL-22 are also considered variants.

Amino acid or nucleotide sequence identity may be evaluated using any of the variety of sequence comparison algorithms and programs known in the art. Such algorithms and programs include, but are by no means limited to, TBLASTN, BLASTP, FASTA, TFASTA, and CLUSTALW (Pearson and Lipman, 1988, Proc. Natl. Acad. Sci. USA 85(8):2444-2448; Altschul et al., 1990, J. Mol. Biol. 215(3):403-410; Thompson et al., 1994, Nucleic Acids Res. 22(2):4673-4680; Higgins et al., 1996, Methods Enzymol. 266:383-402; Altschul et al., 1990, J. Mol. Biol. 215(3):403-410; Altschul et al., 1993, Nature Genetics 3:266-272). In a particularly preferred embodiment, protein and nucleic acid sequence homologies are evaluated using the Basic Local Alignment Search Tool ("BLAST") which is well known in the art (see, e.g., Karlin and Altschul, 1990, Proc. Natl. Acad. Sci. USA 87:2267-2268; Altschul et al., 1990, J. Mol. Biol. 215:403-410; Altschul et al., 1993, Nature Genetics 3:266-272; Altschul et al., 1997, Nuc. Acids Res. 25:3389-3402). The BLAST programs identify homologous sequences by identifying similar segments, which are referred to herein as "high-scoring segment pairs," between a query amino or nucleic acid sequence and a test sequence which is preferably obtained from a protein or nucleic acid sequence database. High-scoring segment pairs are preferably identified (i.e., aligned) by means of a scoring matrix, many of which are known in the art. Preferably, the scoring matrix used is the BLOSUM62 matrix (Gonnet et al., 1992, Science 256:1443-1445; Henikoff and Henikoff, 1993, Proteins 17:49-61). Less preferably, the PAM or PAM250 matrices may also be used (see, e.g., Schwartz and Dayhoff, eds., 1978, Matrices for Detecting Distance Relationships Atlas of Protein Sequence and Structure, Washington: National Biomedical Research Foundation). The BLAST programs evaluate the statistical significance of all high-scoring segment pairs identified, and preferably selects those segments which satisfy a user-specified threshold of significance, such as a user-specified percent homology. Preferably, the statistical significance of a high-scoring segment pair is evaluated using the statistical significance formula of Karlin (see, e.g., Karlin and Altschul, 1990, Proc. Natl. Acad. Sci. USA 87:2267-2268).

The BLAST programs may be used with the default parameters or with modified parameters provided by the user.

Other variants include modifications such as conjugation of other material to IL-22 some examples of which are described above and are also considered functional derivatives of IL-22.

It will be understood by those of skill in the art that numerous and various modifications can be made without departing from the spirit of the present invention. Therefore, it should be clearly understood that the forms of the present invention are illustrative only and are not intended to limit the scope of the present invention.

What is claimed is:

1. A method of increasing insulin sensitivity of a mammal comprising administering to said mammal in need of such treatment a composition, said composition comprising a therapeutically effective amount of a polypeptide consisting essentially of IL-22.

2. The method of claim 1, wherein the polypeptide is recombinantly synthesized.

3. The method of claim 1, wherein the polypeptide consists essentially of human IL-22 or mouse IL-22.

4. A method of enhancing glucose utilization in a mammal comprising administering to a subject in need of treatment a composition, said composition comprising a therapeutically effective amount of a polypeptide consisting essentially of IL-22.

5. The method of claim 4, wherein the polypeptide is recombinantly synthesized.

6. The method of claim 4, wherein the polypeptide consists essentially of human LL-22 or mouse IL-22.

* * * * *